US00PP23576P3

(12) United States Plant Patent
Egger

(10) Patent No.: US PP23,576 P3
(45) Date of Patent: Apr. 30, 2013

(54) ***HEUCHERA* PLANT NAMED 'APPLE CRISP'**

(50) Latin Name: ***Heuchera* hybrid**
Varietal Denomination: Apple Crisp

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 91 days.

(21) Appl. No.: 13/200,484

(22) Filed: Sep. 22, 2011

(65) Prior Publication Data

US 2013/0081183 P1 Mar. 28, 2013

(51) Int. Cl.
*A01H 5/00* (2006.01)

(52) U.S. Cl.
USPC ..... Plt./440

(58) Field of Classification Search ..... Plt./440
See application file for complete search history.

*Primary Examiner* — June Hwu

(74) *Attorney, Agent, or Firm* — Klarquist Sparkman, LLP

(57) ABSTRACT

A new and distinct *Heuchera* plant substantially as shown and described, characterized by very ruffled green leaves with a white veil, compact plant size, and short flowering stalks with small white flowers.

1 Drawing Sheet

Botanical denomination: *Heuchera* hybrid.

Variety designation: 'Apple Crisp'.

Cross reference to *Heuchera* 'Pear Crisp', applied for concurrently U.S. Plant patent application Ser. No. 13/200,483.

BACKGROUND OF THE INVENTION

The present invention relates to a new and distinct cultivar of *Heuchera* and given the cultivar name of 'Apple Crisp'. *Heuchera* is in the family Saxifragaceae. *Heuchera* 'Apple Crisp' originated from a planned cross between *Heuchera* 478-8, a proprietary unreleased plant, as the seed parent, and *Heuchera* 'Amber Waves', (U.S. Plant Pat. No. 13,348) as the pollen parent. Compared to the seed parent, *Heuchera* 478-8, the new cultivar has green foliage rather than brown. Compared to the pollen parent, *Heuchera* 'Amber Waves', the new cultivar has leaves that are smaller more sharply ruffled and are colored green rather than amber to tan, and white flowers rather than cream.

Compared to *Heuchera* 'Pear Crisp' (U.S. Plant patent Ser. No. 13/200,483 applied for concurrently), the new cultivar has green rather than yellow to lime foliage.

Compared to *Heuchera* 'Ruffles', an unpatented plant, the new cultivar has a smaller, tighter habit and smaller, more tightly ruffled leaves.

This new *Heuchera* is distinguished by:

1. very ruffled leaves,
2. green leaves with a white veil,
3. compact plant size,
4. short flowering stalks with small white flowers,
5. excellent vigor.

This new cultivar has been reproduced only by asexual propagation (cuttings and tissue culture). Each of the progeny exhibits identical characteristics to the original plant. Asexual propagation by stem cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 9 month-old *Heuchera* 'Apple Crisp' growing in full sun in the field in September in Canby, Oreg.

FIG. 2 shows the flowers on the same plant.

DETAILED PLANT DESCRIPTION

The following is a detailed description of the new *Heuchera* cultivar based on observations of 2-year-old specimens grown in the ground in the garden in part sun in June in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart, 5th* edition.

Plant:

*Form.*—Basal rosette, herbaceous perennial.
*Hardiness.*—USDA Zone 4 to 9.
*Size.*—14 cm tall from top of the foliage to the ground and 28 cm wide.
*Habit.*—Tight mound.
*Vigor.*—Excellent.
*Roots.*—Fibrous, freely branching, fine, and white in color; roots develop easily from cuttings.

Leaf:

*Type.*—Simple.
*Arrangement.*—Basal.
*Shape.*—Ovate.
*Lobing/division.*—5 main lobes, with 2 to 3 shallow secondary lobes.
*Venation.*—Palmate.
*Margins.*—Crenate and undulate.
*Apex.*—Mucronulate.
*Base.*—Cordate, lobes usually overlapping at the base.

*Blade size*.—Grows to 7 cm long and 6 cm wide.

*Surface texture*.—Top side glabrous, bottom side glandular.

*Petiole description*.—Grows to 7.5 cm long and 1.5 mm wide, glabrous, Yellow Green 145B.

*Leaf color*.—Topside year round Green 137A with a silver veil of Greyed Green 193C, bottom side Yellow Green 147B; venation Green 137A.

Inflorescence:

*Size*.—Grows to 6 cm wide and 22 cm long.

*Type*.—Thyrse.

*Number of flowers per thyrse*.—80 to 100 per thyrse.

*Number of thyrse*.—About 10 in spring bloom.

*Peduncle*.—Grows to 21 cm tall, 2 mm wide at base, Yellow Green 144A, glandular hairs, with 0 to 3 petiolate leaves (ovate, blades grow to 3 cm long and 2.5 cm wide, 5 lobed, margin biserrate, color the same as the leaves).

*Pedicel*.—Variable in size, with glandular hairs, Yellow Green 144A.

*Bloom period*.—Late April to June in Canby, Oreg.

Flower bud:

*Size*.—2.8 mm wide and 4 mm long.

*Description*.—Glandular puberulent, ovoid.

*Color*.—White 155A.

Flower:

*Type*.—Perfect.

*Shape*.—Campanulate.

*Size*.—5 mm long and 4 mm wide.

*Petal description*.—5 in number, 2 mm long and less than 1 mm wide, spatulate with a clawed base, reflexed, tip acute, margin entire, glabrous on top and bottom side, White NN155C on both sides.

*Calyx description*.—4 mm long and 3 mm wide, with 5 lobes, divided ½ way to the base, glandular hairs on outside, glabrous inside, tip obtuse, margin entire, both sides White NN155C with tints of Yellow Green 145C on tips and base.

*Stamen description*.—5 in number, each 2 mm long, White NN155C, anthers Yellow White 158A, no pollen, male sterile.

*Pistil description*.—One central two beaked pistil, 3 mm long, ovary 1 mm long and Yellow White 158C, style 4 mm long, White NN155C.

*Fragrance*.—None.

*Lastingness*.—Each thyrse blooms for about 2 weeks on the plant.

Fruit: None.

Seed: None.

Disease and pest tolerance: No known resistance to *Heuchera* rust, but no problems have been seen. Excellent disease tolerance to powdery mildew. All *Heuchera* are susceptible to root weevils.

I claim:

1. A new and distinct *Heuchera* plant as herein illustrated and described.

* * * * *

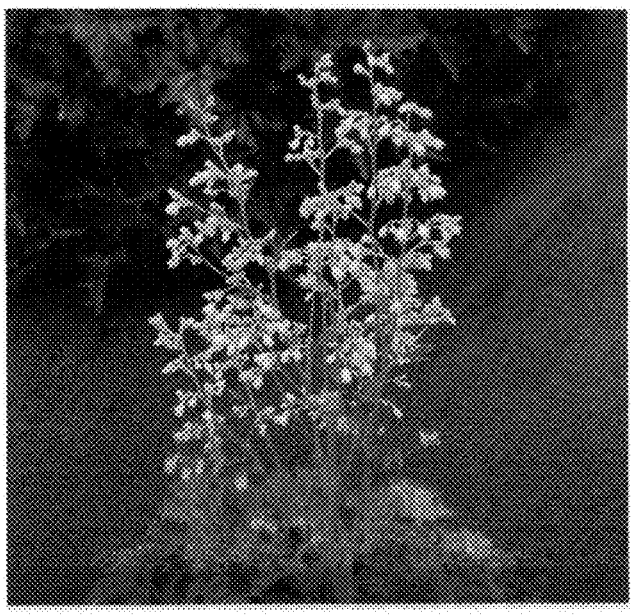

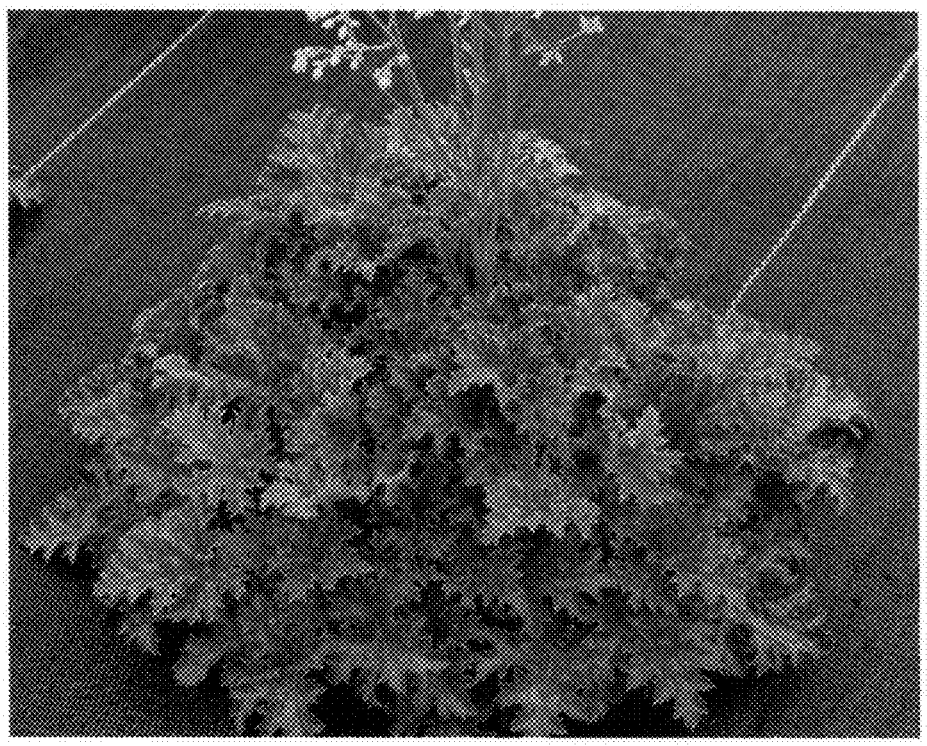
FIG. 1 above, FIG. 2 below